United States Patent [19]
Brinster

[11] Patent Number: 5,858,354
[45] Date of Patent: Jan. 12, 1999

[54] REPOPULATION OF TESTICULAR SEMINIFEROUS TUBULES WITH FOREIGN CELLS, CORRESPONDING RESULTANT GERM CELLS, AND CORRESPONDING RESULTANT ANIMALS AND PROGENY

[75] Inventor: Ralph L. Brinster, Gladwyne, Pa.

[73] Assignee: The Trustees of the University of Pennsylvania, Philadelphia, Pa.

[21] Appl. No.: 345,738

[22] Filed: Nov. 21, 1994

Related U.S. Application Data

[63] Continuation-in-part of Ser. No. 987,250, Dec. 7, 1992, abandoned, which is a continuation-in-part of Ser. No. 802,818, Dec. 6, 1991, abandoned.

[51] Int. Cl.⁶ .......................... A01N 63/00; A61B 17/43; C12N 5/06; C12N 15/01
[52] U.S. Cl. ................ 424/93.7; 424/93.1; 424/93.2; 424/93.21; 435/172.3; 600/33; 604/906; 800/2; 800/DIG. 4; 800/DIG. 5
[58] Field of Search .............................. 800/2; 435/172.3; 424/93.1, 93.2, 93.21, 93.7; 600/33; 604/906

[56] References Cited

FOREIGN PATENT DOCUMENTS 8809816  12/1922  WIPO .

OTHER PUBLICATIONS

Brinster et al Cell 59: 239, 1989.
Hochim et al Annual Biotechnology 1(1):21, 1990.
Krimperfet et al Embo J 6(6): 1673, 1987.
Cauglon in New Scientist, 25 Nov. 1995, pp. 14–15.
Marshall Science 270: 1751, 1995.
Orbin & Matuesty *Report & Reumunodolins of the Barel to Asers the NIH Inventions in Research in gene Therapy*, Dec. 7, 1995.

*Primary Examiner*—Brian R. Stanton
*Attorney, Agent, or Firm*—Oblon, Spivak, McClelland, Maier & Neustadt, P.C.

[57] ABSTRACT

An animal harboring a non-native germ cell, its corresponding line, and the corresponding germ cells, are obtained by colonizing the testis (or testes) of a host animal with primitive cells followed by raising and/or breeding the host.

15 Claims, 6 Drawing Sheets

REPOPULATION OF TESTICULAR SEMINIFEROUS TUBULES WITH FOREIGN CELLS, CORRESPONDING RESULTANT GERM CELLS, AND CORRESPONDING RESULTANT ANIMALS AND PROGENY

This application is a Continuation-in-Part of application Ser. No. 07/987,250, filed Dec. 7, 1992, now abandoned which is a Continuation-in-Part of application Ser. No. 07/802,818, filed Dec. 6, 1991, abandoned.

The research on which the technology described in this document is based was supported by U.S. government funding. The present invention is based on work in part funded by the National Institutes of Health (HD 23657).

BACKGROUND OF THE INVENTION

1. Field of the Invention

The present invention relates to animals harboring a non-native germ cell, to corresponding animal lines and germ cells, and to methods for obtaining the same.

2. Discussion of the Background

There have been many attempts to influence differentiation of developing cells by modifying the genotype of an embryo and then observing its effect on the phenotypic development pattern in the progeny. These techniques included transgenic methods (Brinster et al, Harvey Lectures, 80:1–38 (1986) nuclear transfer (McGrath & Solter, Science (1983) 220:1300–1302) and cell-egg fusions (Graham, "Heterospecific Genome Interaction," 1969 Wistar Institute Press, pp. 19–35, ed. Defendi). Of these, the latter two have had limited success.

Another approach might be to add a stem cell(s) to an early embryo and determine its effect on development. For example, one might imagine that a stem cell from bone marrow would contribute to the population of, and thus modify the differentiation of the evolving bone marrow cells in the host embryo. To pilot these experiments, older embryo cells were introduced into young embryos resulting in modest success with colonization (Moustafa & Brinster, J. Exp. Zool. (1972) 181:193).

These initial experiments were followed by studies using bone marrow stem cells and teratocarcinoma stem cells (also called embryonal carcinoma cells). There was evidence that both these cells colonized the developing embryo (Brinster, J. Exp. Med. (1974) 140:1049–1056). In the case of the embryonal carcinoma (EC) cell, the colonization was demonstrated dramatically by a change in the color of hairs in the coat of the mouse. This was an exciting result which stimulated a great deal of interest among scientists in the field, because it showed the possibility of colonizing an animal with non-embryo cells. This would provide a means to introduce new genetic information through the DNA of the colonizing cells.

The next year these results were confirmed and extended by two other laboratories (for work done in one of these laboratories, see Mintz & Illmensee, Proc. Nat. Acad. Sci. (USA) (1975) 72:3585–3589) and it was demonstrated that the introduced EC cells may colonize numerous tissues including germ cells (sperm and eggs). Thus, a gene that was mutated, modified, or added to the cell in vitro could eventually end up in sperm or eggs of an animal, creating a new genetic strain of mice.

Unfortunately EC cells colonized the germline poorly and a better cell line was sought. In 1981 two scientists, Gail Martin and Martin Evans, independently described a more efficient cell designated the embryonic stem (ES) cell (Martin, Proc. Nat. Acad. Sci. (USA) (1981) 78:7634; Evans & Kaufman, Nature (1981) 292:154). These cells colonize the germline better than EC cells. However, it seems likely that they arise from the same pool of primitive cells in the embryo and are quite similar in biological characteristics.

Embryonic stem cells can be modified in vitro (in culture flasks) by adding genes or changing endogenous genes and then the modified cells introduced into a blastocyst where they participate in development and can become sperm. This technique allows very specific modification of the mouse genome and perhaps other species.

Techniques for obtaining non-human transgenic animals through the injection of DNA into eggs are also known. See e.g., Gordon et al, Proc. Nat. Acad. Sci. (USA), (1980) 77:7380–7384. These techniques however, as well as the use of ES cells noted above, are very labor intensive.

Gene therapy is by definition the insertion of genes for the purpose of medicinal therapy. The principle underlying gene therapy is to, rather than deliver doses of one or more pharmacologic molecule, deliver a functional gene whose RNA or protein product will produce the desired biochemical effect in the target cell or tissue. The genes may be delivered into endogenous cells or within new cells delivered to the animal. There are several potential advantages of gene therapy over classical biochemical pharmacology, including the fact that inserted genes can produce extremely complex molecules, including RNA and proteins, which can be extraordinarily difficult or impossible to administer and deliver themselves.

The many applications of gene therapy, particularly via stem cell genetic insertion, have been extensively reviewed (see, Boggs et al., Int. J. Cell Cloning (1990) 8, 80; Kohn et al., Cancer Invest. (1989) 7, 179; Lehn, Bone Marrow Transpl. (1990) 5. 287; and Verma et al., Scientific Amer. (November 1990) 68). Genetically transformed human stem cells have wide potential application in clinical medicine, as agents of gene therapy.

Methods and compositions are known for the ex vivo replication and stable genetic transformation of animal, including human, stem cells and for the optimization of such stem cell cultures. The applications of gene therapy could be advantageously expanded if techniques were available for the application of gene therapy to animal primitive germ cells.

SUMMARY OF THE INVENTION

Accordingly, it is an object of this invention to provide a facile method for obtaining animals harboring a biologically functional non-native, preferably male, germ or stem cell, and for obtaining corresponding resultant germ or stem cells.

It is another object of this invention to provide a facile method for obtaining new animal lines, and for obtaining corresponding resultant germ or stem cells.

It is another object of this invention to provide animals harboring a biologically functional non-native germ or stem cell, their progeny, and corresponding resultant animal lines and germ or stem cells.

It is another object of this invention to use as said non-native germ cell, one or more animal stem cells which has been cultured maintained and/or expanded in culture ex vivo.

It has been discovered by the inventor that the above objects and other objects which become apparent from the description of the invention given hereinbelow are satisfied by the following method. Primitive germ cells are obtained and are optionally expanded and/or modified ex vivo. The testis (or testes) of a male animal host is (are) repopulated with at least one primitive cell (e.g. a totipotent stem cell) which is not native to the host. Because the donor cell(s) is (are) stem cells, they can expand to repopulate the seminiferous tubules of the recipient testis. The recipient animal may then be bred to obtain a novel animal line in which every cell of the descendant animal is genetically non-native to the original recipient host animal. The methods of the present invention have now been successfully used to produce progeny that contain genetic information different from the biological sire (father). That is, the genetic information in the progeny is that of the donor stem cell and not that of the recipient male which is the natural (biological) sire.

BRIEF DESCRIPTION OF THE FIGURES

FIG. 1 is a control. FIG. 2 comes from a transgenic (ZFlacZ) mouse in which late stages of spermatogenesis stain blue and hence can be used as a marker for stem cell differentiation to mature spermatozoa. FIG. 2 shows intense blue (dark) staining in all mature stages of spermatogenesis, which occupy the center of the tubule. Control FIG. 1 does not. Stem cells taken from an animal carrying the ZFlacZ transgene (FIG. 2) will stain blue if they are transferred to a recipient, survive and differentiate into spermatozoa. Staining does not occur in the cells of the recipient male, because it does not carry the marker transgene ZFlacZ.

FIG. 3B is a higher magnification view of the tubules shown in FIG. 3A. FIGS. 3C and D likewise show blue (dark) stained tubules.

FIGS. 4A and B are photographs demonstrating spermatogenesis in the testis of a recipient male following transfer of ZFlacZ donor cells. A) Testis from (C57Bl/6 x SJL) F1 Busulfan®-treated male 6 months after donor cell transfer. Note active spermatogenesis and mature spermatozoa. Round spermatids and more mature stages stain blue. When stain is intense, immature stages also appear blue. B) Tubules from epididymis of mouse with testis shown in A). Many mature spermatozoa appear as red dots in lumen of the tubules. Background blue color in the lumen is the result of β-galactosidase (transgene) activity arising from the cytoplasm of immature sperm cells. Mature spermatozoa do not stain for β-galactosidase because they lack sufficient cytoplasm. Stain: X-gal followed by neutral fast red. (A x 280; B x 125)

FIGS. 5A and B are photographs of testis of Busulfan®-treated recipient male injected with ZFlacZ donor cells 14 months previously. A) Gross appearance. The testis is approximately 80 percent normal size, because an inadequate Busulfan® effect permitted the reinitiation of spermatogenesis from endogenous stem cells (unstained tubules). Blue tubules indicate spermatogenesis from ZFlacZ donor spermatogonial stem cells. Testes has been partially transacted longitudinally to allow for penetration of fixative and stain (X-gal). Scale bar 1 mm. B) Microscopic appearance. Blue tubule cross sections represent spermatogenesis from donor stem cells. Red tubule cross sections reflect spermatogenesis from endogenous stem cells. The ratio of blue to red tubules across several complete testes cross sections in this area was approximately 1:12. Other areas of the testis have fewer blue tubules. Stain: X-gal followed by neutral fast red (x 70);

FIG. 6 are testes from progeny of the recipient male described in FIG. 5. The testis on the left stained blue with X-gal indicating the presence of the transgene in all cells. The testis on the right is from another offspring and is not blue because it does not contain the transgene. The seminiferous tubules of the parent male displayed a mosaic pattern of staining resulting from donor stem cell and endogenous stem cell areas of spermatogenesis (See FIG. 5). Age of progeny approximately 10 weeks. Born 11 months following donor cell transfer. Scale bar 0.25 cm.

DETAILED DESCRIPTION OF THE PREFERRED EMBODIMENTS

According to the present invention, primitive cells (e.g., spermatogonial stem cells) are introduced into prepared seminiferous tubules of animal testis (or testes). There, the introduced primitive cells develop into mature spermatozoa. This colonization is possible because the lumen of the seminiferous tubule is an immunologically privileged site and provides the proper environment. Evidence for this is the absence of endogenous antibody specific to sperm, and the presence of T-cells that are tolerant to spermatozoa in the circulating blood of males. Furthermore, injection of sperm into the tissues of a male generally provokes an immunological response.

Cells which can develop into more differentiated cells of two or more types are used as the primitive cells. Thus, one of two types of cells can be used: (1) totipotent cells, which are cells having the potential to differentiate into any cell type, including germ cells (e.g., spermatogonial stem cells); and (2) pluripotent cells, which are cells capable of differentiating into two or more types of cells, e.g., bone marrow stem cells, liver stem cells, kidney stem cells, etc.

An illustrative procedure for repopulating the testis (or testes) of a host is as follows. A male host animal is prepared by destroying the native germ cell population in the seminiferous tubules by a method that leaves intact (i.e., biologically functional) the supporting cells, including the Sertoli cells. Suitable known methods include physical means (e.g. radiation[1], heat[2], etc.), chemical means (e.g. cadmium[3], Busulfan®[4], etc.), but any other known techniques to selectively destroy native sperm cells can be used. Preferably radiation is used, with Busulfan® being a useful chemical method.

[1]Withers et al, *Radiation Res.* (1974) 57:88–103.
[2]Gasinka et al, *Neoplasma* (1990) 37(3) :357–366
[3]Parizek, *J. Reprod. Fert.* (1960) 1:294–309
[4]1,4-Butanediol dimethylsulfonate esters; e.g., 1,4-bis(methanesulfonyloxy)butane; 1,4-di(methanesulfonyloxy)butane; 1,4-di(methylsulfonyloxy)butane; methanesulfonic acid tetramethylene ester; tetramethylene bis(methane sulfonate). See Bucci et al, *Mutation Res.* (1987) 176:259–268.

The amount of native germ cell population destroyed by the above techniques may be varied depending on the outcome desired (e.g., partial replacement or full replacement of endogenous spermatogenesis). Some applications of the invention may be best served by partial replacement (see below). In a first embodiment, the total native germ cell population is destroyed to ensure that every offspring sired by the recipient male will be genetically identical to the donor animal. In a second embodiment, less than the total (e.g., between 10 and 90%) of the native germ cell population of the recipient male is destroyed. In this second embodiment, the recipient male will produce both offspring which are genetically identical to itself as well as offspring genetically identical to the donor animal.

A typical Busulfan® treatment is illustrated as follows. Forty milligrams of Busulfan® are dissolved in 5 ml of dimethylsulfoxide, to which 5 ml of water are then added. An aliquot of this solution is injected intraperitoneally into a mouse in an amount sufficient to administer a dose of 1 mg of Busulfan® per 25 g (40 mg/kg) of mouse weight (Bucci et al, *Mutation Res.* (1987) 176:259–268). The male is then allowed to recover, and tested to ascertain that there is no remaining spermatogenesis by breeding and/or testicular biopsy.

Alternatively, in mice receiving lower dose of Busulfan® (e.g., either purposeful by the researcher or by reason of leakage at the time of injection), tubules will repopulate with both the transferred germ or stem cell line as well as with surviving endogenous stem cells.

Alternatively, one can employ a male host that genetically has low numbers or no sperm in its testes, such as inbred strains of mice that produce offspring with seminiferous tubules depleted of sperm cells. For example, the sperm cells of so-called W-mutant mice are deficient for an enzyme necessary for their survival and proliferation. Homozygotes and compound heterozygotes for certain alleles of this gene are so deficient for this enzyme that they are completely devoid of sperm cells when adult. C57BL/6J mice segregating the $W^v$ and $W^{44}$ alleles, WB/ReJ mice segregating the W allele, and 129/SV mice segregating the $W^{54}$ allele can be maintained and bred toward this end. For example, a C57BL/6J $W^v$/+ animal bred to a WB/ReJ W/+ will yield a proportion of hybrid W/$W^v$ males, which when mature will totally lack sperm cells. The testes of these hybrids may accept donor cells from C57BL/6J mice or WB/ReJ mice without histocompatibility problems.

If necessary, tolerance in the recipient can be induced by transferring cells corresponding to those primitive cells being transferred to the testis (or testes) of the host, to the thymus of the host before transfer of the primitive cells to the testis (or testes). Thus if spermatogonia is the primitive cell being transferred to the testis (or testes) of the host, spermatogonia may be first transferred to the thymus of the host to induce tolerance. See, Posselt et al, *Science* (1990) 249:1293–1295.

Alternatively, cells from an animal of the same strain as the recipient host can be used, or an immunodeficient host can be used. For an example of the latter, inbred strains of mice (e.g. SCID mice or nude mice) bred to act as recipients of sperm cells can be used. As an example of the former C57 mice segregating the c (albino) and C (color) allele can be maintained. Homozygotes and compound heterozygotes for these alleles are easily distinguished by coat color. A Busulfan®-treated homozygote for the one allele can receive donor cells from a homozygote for the other allele. If the recipient animal thereafter gives rise to offspring showing the donor-type coat color marker, this is evidence that the donor cells gave rise to functional sperm.

The primitive cells used in accordance with the invention can come from other individuals (including both the same and other species) or in vitro culture. The primitive cells may be harvest from a fetus in its third trimester, a newborn, a preadolescent, a fertile individual, an older individual who is clinically infertile but is still producing primitive cells, or a recently deceased individual provided the primitive cells are isolated prior to cell death (the cells are preferably isolated within 2 hours of death). Examples of primitive cells that can be used include totipotent stem cells, embryonal carcinoma cells, embryonic stem cells, sperm cells from other males (e.g. juvenile males with high levels of primitive sperm cell types), primordial germ cells, other primitive cells, etc. Primitive sperm cells from seminiferous tubules, embryonic stem cells grown in culture, or primitive cells from body organs are prime candidates. The use of female (XX) cells is also within the scope of the present invention.

These primitive cells may be obtained in accordance with known procedures. For example, spermatogonia stem cells may be obtained as follows. The testis of a neonatal animal is collected and the covering removed. The tubules are enzymatically-digested to produce a single-cell suspension which contains approximately 15% stem cells. Besides such spermatogonial stem cells found in neonatal and adult testis, there are several other known sources of suitable cells. Stem cells from a tissue culture, such as embryonic stem and embryonal carcinoma (teratocarcinoma) cells are easily utilized. Other desirable cells are primitive cells from organs which have the potential to regenerate, such as the liver, or lymphoid organs, such as the bone marrow.

Alternatively, primitive cells may be obtained by a testicular biopsy in order to preserve the fertility of the donor animal.

When the primitive cells are cultured prior to implantation, the primitive cells may be maintained and/or expanded in a culture media using known techniques. A suitable culture medium would be Dulbecco's modified Eagle's Medium (DMEM) plus 15% fetal calf serum. Other culture medium containing higher levels of pyruvate and lactate (See Brinster, In: Growth, Nutrition and Metabolism of Cells in Culture, Vol. II, Ed. Rothblat & Cristofalo, (1972), 251–286, Academic Press). Primitive male germ cells should be cultured at 32° C. because of their sensitivity to high temperature. Other cells could be cultured at higher temperature depending on individual characteristics (e.g., chicken cells at 37–42° C.). Various growth factors, such as stem cell factor, basic fibroblastic growth factor, leukemia inhibitory factor, and others could be used to enhance cell proliferation. A gas composition of 0–10% $CO_2$ in 90–80% air could be used. However, variations in concentrations of $O_2$ might be applicable for some stages of culture. The period of culture could be short (<1 hr) or indefinite depending on the application envisioned. In addition, the cells could be frozen at –196° C. (liquid nitrogen) with cell cryopreservation techniques for a period of time before, during or after culture and prior to reintroduction into a recipient testis.

Cell densities which may be used are of from $10^4$ to $10^9$ cell per ml of culture medium. The medium used to culture the primitive cells may comprise three basic components. The first component is a general media component, the second is a serum component and the third is a special factor component. Standard known media components such as, for example, IMDM, MEM, DMEM, RPMI 1640, Alpha Medium of McCoy's Medium can be used and can contain combinations of serum albumin, cholesterol and/or lecithin, selenium and inorganic salts.

The serum component may be present in the culture in an amount of at least 1% (v/v), based on the volume of the medium. The serum concentration is preferably about 15% (v/v). Standard serum can be used such as horse serum, human serum, fetal calf serum, newborn calf serum, etc. Alternatively, the serum component can be replace by any of several standard serum replacement mixtures which typically include insulin, albumin, and lecithin or cholesterol (See, Iscove et al., Exp. Cell Res. (1980) 126, 121 and Dainiak et al., J. Clin. Invest. (1985) 76 1237).

Glucose concentration is usually maintained in the range of about 5 to 20 mM. Lactate concentration is usually maintained 5 mM or above. Glutamine concentration is generally maintained in the range of from about 1 to 4 mM. Ammonium concentration is usually maintained below about 2.4 mM. The concentrations can be monitored by either periodic or on-line continuous measurements using known methods. See, e.g., Caldwell et al., J. Cell. Physiol. (1991) 147, 344.

Suitably, the cell cultures may be supplemented with various growth factors as described, e.g., in U.S. Pat. No. 5,199,942 (Gillis et al.). Ideally, the cell cultures are supplemented with at least one cytokine such as an interleukin 1–6 (IL 1–6), GM-CSF, erythropoietin (EPO), mast cell growth factor (MCGF), basic fibroblast growth factor, transforming growth factor β (TGF-β), platelet derived growth factor (PDGF), epidermal growth factor (EGF), etc.

Culturing is typically carried out at a pH which is roughly physiologic, i.e. 7.0 to 7.6.

The nutrient media of the present invention can be exchanged three times weekly, either as single exchanges or a one-half medium and serum exchange. Alternatively, the nutrient media of the present invention can be replaced continuously or periodically.

Following culturing, the cells may be isolated by trypsin digestion and prepared for transfer by centrifugation and resuspension in concentrated form ($10^6$–$10^8$ cells/ml).

In a preferred embodiment the cells and/or tubules are modified to facilitate the colonization as well as diversity of cells that are effective. For example, the primitive cells may be added with their corresponding Sertoli cells to facilitate population, the surface of the primitive cells may be treated with phytohemagglutinin (PHA) to make the primitive cells more adherent (Mintz et al, *Dev. Biol.* 31:195–99), or the primitive cells may be added with corresponding "carrier" sperm cells to facilitate repopulation. Alternatively the tubules can be subjected to a limited enzymatic digestion to render them more accessible to the transferred primitive cells.

In an optional embodiment of the invention, the primitive cells are modified genetically by any of a variety of known techniques[5] so that the genetic characteristics of the resulting spermatozoa can be predetermined. The primitive cells which are used in accordance with this embodiment of the invention may also be native cells possessing naturally induced mutations or variations or native cells possessing artificially induced mutations or variations.

[5]See, e.g., Lovell-Badge, "Teratocarcinoma and Embryonic Stem Cells: A Practical Approach", IRL Press (1987), ed. Robertson, or Capecchi, *Science* (1989) 244:1288–1292.

The primitive cells of the present invention can be modified in vitro by a variety of techniques (e.g., see Gene Targeting: A Practical Approach, A. Joyner (1993), IRL Press. Genes which may be used with this embodiment include genes containing a DNA sequence (or the corresponding RNA sequence may be used) encoding an intracellular, secreted, or cell surface molecule which is exogenous to the animal donor. Exogenous, in this context, means that the animal host either lacks a properly functioning gene sequence or lacks the gene entirely.

Alternatively, vectors can be used to express the gene. Suitable vectors containing the DNA sequence (or the corresponding RNA sequence) which may be used in accordance with the invention may be an eukaryotic expression vector containing the DNA or the RNA sequence of interest. Techniques for obtaining expression of exogenous DNA or RNA sequences in a host or cell are known. See, for example, Korman et al, Proc. Nat. Acad. Sci. U.S.A. (1987) 84, 2150.

This vector, as noted above, may be administered to the germ or stem cell being cultured in a retroviral or other viral vector (i.e., a viral vector) vehicle, a DNA or RNA/liposome complex, or by utilizing DNA-mediated gene transfer. Further, the vector, when present in non-viral form, may be administered as a DNA or RNA sequence-containing chemical formulation coupled to a carrier molecule which facilitates delivery to the host cell. Such carrier molecule would include an antibody specific to the cells to which the vector is being delivered or a molecule capable of interacting with a receptor associated with the target cells.

Cell-mediated gene transfer may be used in accordance with the invention. In this mode, one relies upon the delivery of recombinant genes into living organisms by transfer of the genetic material into cells derived from the host and modification in cell culture, followed by the introduction of genetically altered cells into the host. An illustrative packaging cell line which may be used in accordance with this embodiment is described in Danos et al, Proc. Natl. Acad. Sci. U.S.A. (1988) 85, 6460.

The retroviral vector vehicles used in accordance with the present invention comprise a viral particle derived from a naturally-occurring retrovirus which has been genetically altered to render it replication defective and to express a recombinant gene of interest in accordance with the invention. Once the virus delivers its genetic material to a cell, it does not generate additional infectious virus but does introduce exogenous recombinant genes to the cell.

In other viral vectors, the virus particle used is derived from other naturally-occurring viruses which have been genetically altered to render them replication defective and to express recombinant genes. Such viral vectors may be derived from adenovirus, papillomavirus, herpesvirus, parvovirus, etc.

The molecules which may be used in accordance with this invention include genes encoding immune stimulants such as Class I histocompatibility genes, Class II histocompatibility genes, bacterial genes including mycobacterial (PPD) genes, genes encoding heat shock proteins, viral glycoproteins encoding genes including vesicular stomatitis virus G protein, influenza hemagglutinin, and herpes virus glycoprotein β, minor histocompatibility antigens; genes encoding growth stimulants/inhibitors including inducers of differentiation such as stimulants, including interleukin-2 (IL-2) IL-4, 3, 6 or 8, inhibitors/inducers of differentiation, such as TNF-α or β, TGF-β (1, 2 or 3), IL-1, soluble growth factor receptors (PDGF, FGF receptors), growth factors and analogs (PDGF, FGF), interferons (α, β or γ), adhesion molecules, etc.; gene encoding selectable markers including thymidine kinase, diphtheria toxin, pertussis toxin or drug-sensitive proteins.

The DNA/RNA sequence is preferably obtained from a source of the same species as the animal recipient, but this is not absolutely required, and the present invention provides for the use of DNA sequences obtained from a source of a species different from the donor or recipient animal in accordance with this embodiment.

These genes are suitably operably linked to appropriate elements including promoter, enhancers, repressors, etc. Techniques known in the art can be used to select suitable elements and to operably link them to the above genes.

The selected primitive cells are then introduced into the individual tubules. For example, a prepared male can be anesthetized and the testis (or testes) surgically exposed. By micromanipulation methods a thin glass needle is introduced into exposed tubules, one after another, and each tubule is injected with a solution containing the primitive cells being used to colonize the tubule. Alternatively, the primitive cells can also be introduced by injecting into other parts of the tubular system e.g. the lumen of the rete testes. To inject the rete testes one may use either fine stainless-steel needles or fine pulled-glass capillaries loaded with donor primitive cells. A micromanipulator is used to direct the tip of such an instrument to penetrate the rete testis or the seminiferous tubule. The cells are expelled and will back-fill the seminiferous tubules.

In a preferred embodiment, to minimize the number of injection sites and to increase the efficiency of injection of a concentrated primitive cell suspension, a glass pipette with a 1 mm outside diameter and a 40 $\mu$ tip is secured into a micropipette holder. The tip of a 1 ml plastic syringe can then be inserted into the other end of the micropipette holder, and the syringe cut at about the midlength mark. The cell solution containing the primitive cells is then deposited in the syringe barrel, which is then screwed onto the metal end of an Eppendorf capillary holder attached by tubing to a pressure injector. To expose the tubules, only 1 to 3 small incisions (1–3 mm) need be made in the tunica per testis. using this embodiment, an average of 80 percent of the surface tubules can be filled with concentrated cell suspension.

The cell suspension of primitive cells suitably comprises an injection medium and primitive cells (e.g., $10^6$–$10^8$ cells per ml). For example, the injection media can comprise NaCl, $Na_2HPO_4$, KCl, $KH_2PO_4$, EDTA, pyruvate, lactate, glutamine, glucose, bovine serum albumin, and DNAse I. The pH of the injection media is suitably in the range of 7–7.7, preferably 7.4.

Other systems may also be suitably used for introduction of the cells. These include injection into the vas deferens and epididymis or manipulations on fetal or juvenile testes, techniques to sever the seminiferous tubules inside the testicular covering, with minimum trauma, which allow injected cells to enter the cut ends of the tubules. For example, a fine surgical thread is circled about a number of tubules, and then drawn tight, severing the tubules. A donor-cell suspension is then injected into the testis.

Alternatively neonatal testis (or testes), which are still undergoing development, can be used. Here, a surgical procedure to expose the neonatal testis (or testes) for injection of new cells is used. Neonatal mice are chilled on ice for anesthetization. The tiny testes are surgically exposed, and a small bladed-instrument is used to disrupt the tubular architecture. Donor cells are injected, and become incorporated during repair. These cells then participate, with endogenous cells, if present, in the maturation of the testis.

As noted supra, the primitive cells entering the tubule are generally protected from destruction by the immunologically privileged environment of the internal lumen of the tubule. Cells that leak from the tubule are typically destroyed by the immune system of the host since the cells are foreign to the animal.

The destruction of cells outside the tubule lumen is desirable because primitive stem cells have a high propensity to undergo transformation into malignant growths. But if this undesirable property is eliminated from the primitive cells then destruction of primitive cells outside the site of colonization could be unimportant.

In an embodiment of the invention, one can use animal strains tolerant towards cells from antigenically different animals of the same or different species. For example, nude mice, having no thymus-derived cells, and SCID mice (Bosma et al, *Ann. Rev. Imm.* (1991) 9: 323–50), having low levels of both B-cells and T-cells, can be used as recipients.

In another embodiment of the invention, one can use animal strains which are from different species to provide donor cells (xenogeneic transfer). Donor cell-derived spermatozoa then may be mature along with endogenous spermatozoa in the epididymis. The egg of the foreign species would provide the specificity of spermatozoal selection during in vitro or in vivo fertilization. For example, if the donor is a chicken and the recipient male is a mouse, the spermatozoa collected from the mouse, when reintroduced into a fertile chicken would result in chicken progeny. Chicken represent an important species for xenogeneic transfer because they are economically an efficient source of quality protein and testicular spermatozoa placed in the chicken oviduct are capable of fertilizing the egg (Jones, et al., in "Oxford Reviews in Reproduction Biology," ed. Milligan, D. R. (Oxford University Press, England), 1993, vol. 15, pp 233–264).

Results of the introduction of the primitive cells are monitored after recovery of the males from the implantation procedure. As is known, depending on the species of the animal used, the period for spermatogenesis is approximately 30 to 60 days, and another 10 to 15 days is needed for epididymal maturation of spermatozoa. See, e.g., "Reproduction in Domestic Animals", 4th ed., Acad. Press (1991), ed. P. Cupps. Therefore, depending on the species used, males that have received primitive cells in accordance with the invention can be examined beginning about two months after cell transfer.

The present invention is applicable to any species of animals, including human, in which the male has testes, including but not limited to transgenics. The invention is also not limited to mammalian species. It can be used to provide animals and animal lines of many types with a single, or many, novel genetic modification(s) or novel characteristic(s). The animals to which the present invention can be applied include animals, such as rodents (e.g., mice, rats, etc.), birds (such as chickens and turkeys), wild and zoo species (such as zebras, lions, pandas, giraffes, polar bears, monkeys, sea otters, etc.) which can be modified to permit their use in cellular diagnosis or assays. The present invention may also be advantageously applied to farm animals such as domesticated ruminants or fowl (e.g., cattle, chickens, turkeys, horses, swine, etc.), to imbue these animals with advantageous genetic modification(s) or characteristic(s).

The donor and recipient animal can be the same animal patient. In this case, primitive cells are collected from the animal patient prior to destruction of the germ cell population and then reintroduced thereafter. This embodiment would preserve the ability of the animal patient to reproduce following radiation therapy, for example which may be necessary as a cancer treatment. Alternatively, spermatogonial stem cells may be harvested from the animal or patient and kept in culture or frozen. Then when progeny are desired, the stem cells are transplanted to a recipient mouse testes. The donor animal or patient species egg could then be fertilized by spermatozoa developed in the recipient mouse testes. There are no time constraints since the stem cells continually undergo self-renewal.

Once an initial fertilization event is achieved and the resulting offspring is fertile, the animal line with its novel genetic modification or characteristic is established, with the novel genetic modification or characteristic being present in both male and female offspring. Thus, in accordance with the invention one may produce an animal harboring, in its testes only, a biologically functional germ cell which is not native to that animal by repopulating its testicular seminiferous tubules. This (parent) animal can produce progeny. Every cell in the progeny is genetically non-native as compared to the parent animal.

Both the parent animal and its progeny provided by the present invention have very varied uses, including uses in agriculture and biomedicine, including human gene therapy. An illustrative agricultural use of the present invention relates to increasing the breeding potential of a valuable stud animal. In this use, a testicular biopsy from a valuable stud animal is used to obtain stem cells for transfer into the treated (with either Busulfan®, radiation, etc.) testes of a recipient animal. The recipient animal thereafter produces sperm which are genetically from the valuable stud and natural matings with this recipient male provide an alternative to artificial insemination with ejaculates from the valuable stud. This illustrative technique is particularly useful as insurance against an illness, injury or the death of a valuable stud animal. Likewise, spermatogonial stem cells of valuable animals may be harvested by biopsy from the testes and expanded in a mouse testes or in culture and subsequently frozen. The spermatogonial transplantation invention provides for immortalization of the genetic composition (original or modified) of any male individuals of any species. This ability will revolutionize the biology of inheritance.

Another illustrative application of the present invention is its application to create (chimeric) animals useful in either biomedicine or agriculture. The present invention provides an advantageous complementation to existing transgenic techniques.

Existing transgenic techniques, when applied to animals other than laboratory mice, are often hampered by the difficulty of recovering embryos, differing characteristics in embryos of different species, a lack of knowledge about the specifics of reproductive timing in the given species, the economics of current techniques, etc. The present invention permits the difficulty and expense of embryological transgenic work to be by-passed.

In accordance with the present invention, spermatogonia stem cells can be genetically modified and then transferred to recipient testes. The valuable genetic traits present in the resultant germ cells can be passed onto the (transgenic) progeny of the recipient stud. This particular application of the present invention is particularly important to the genetic engineering of large agricultural animals.

The present invention also has applications in gene therapy, including human gene therapy. For example, a patient with a deleterious genetic trait could undergo a testicular biopsy. Isolated stem cells can be genetically modified to correct the deleterious trait. The patient then undergoes a treatment to remove the remaining germ cells from his testes, for example by specific irradiation of the testes. His testes (now devoid of germ cells) can then be recolonized by his own, genetically-corrected, stem cells. The patient can then father progeny free from the worry that he would pass on a genetic disease to his progeny. Alternatively, the stem cells with the corrected gene could be transplanted to a mouse and the resulting sperm used for fertilizing eggs, thereby foregoing the use for reimplanting stem cells into the original human testis.

Conventional cell markers, such as surface antigens or internal enzymes, can be employed in the transferred primitive cells to facilitate detecting their presence in biopsy specimens of the testes. The presence in the ejaculate of spermatozoa with the characteristics of the marker is a reliable indication of success. Thus, in accordance with a preferred embodiment, at least one genetic marker is preferably used to distinguish the introduced cells from residual sperm that might arise from the host male. For example, transgenic mice strains that can produce a characteristic stain in sperm cells which serve as donor marker cells can be used. The promoter from a gene active in developing sperm cells (Zfy-1 or a homolog) is used to drive expression of the gene for the bacterial enzyme beta-galactosidase (lac Z) in transgenic mice. In the presence of the reagent X-gal, sperm cells from these transgenic mice stain blue, unlike those from normal mice. Thus, when acting as donors, the cells can be easily distinguished from host cells, serving as a marker for analysis.

Co-insertion of both a gene of interest and a marker gene into stem cells to be used as donors may be carried out in accordance with the following illustration. The Zfy-1/beta-galactosidase construct described above is mixed in solution with a genetic construct of interest to either co-inject into eggs to produce transgenic mice to provide eventual donor cells or transfect into tissue culture cells to be used as donors. A proportion of the resulting animals or cell lines will contain both constructs, providing donor cells with an easily-detectible marker as well as the gene of interest.

Since colonization usually only takes place in some tubules, low numbers of spermatozoa can result. However, any male in which some transferred primitive cells have developed into mature spermatozoa is useful in accordance with the invention since a variety of conventional techniques exist to achieve fertilization in animals with low sperm numbers. These techniques include, but are not limited to: hormonal treatment, abstinence, artificial insemination, in vitro fertilization, zona drilling, and microintroduction of sperm into the egg.

The experiments described below, which are provided for purposes of non-limiting illustration of some embodiments of the invention, demonstrate the survival, differentiation and development to enter stages of spermatogenesis of cells transferred in accordance with the invention and the cross-strain utility of the invention, and thereby provide strong evidence of the cross-species potential of the present invention.

EXAMPLES

Example A

Introduction

Foreign potential stem cells for transfer were isolated from the testes of very young male mice, usually between 3 to 10 days of age. These cells carried a reporter or marker gene encoding the *E. coli* β-galactosidase (lacZ) gene. This gene is not normally present in the mouse genome. However, if a cell contains the gene, it will make the enzyme β-galactosidase. In the presence of the reagent X-gal, the cell will then stain blue. In addition, the transgene in these cells will only be active in late stages of spermatogenesis, in the round spermatid and later stages, because the lacZ structural gene is under control of a promoter or activating DNA sequence designated ZF. These late stages of spermatogenesis are not present in the neonatal testes. Therefore the transgene is not active in neonatal testes and these cells cannot be stained blue nor do any of the cells have the appearance of mature spermatozoa at this early age. As a result of this experimental procedure, the transferred cells must not only survive, but they must undergo differentiation and development to become late stages of spermatogenesis in order to stain blue. Furthermore, the transferred cell descendants can easily be distinguished from any endogenous sperm cells of the recipient host mouse (should any be present), because these endogenous cells will not stain blue.

Figure 1:
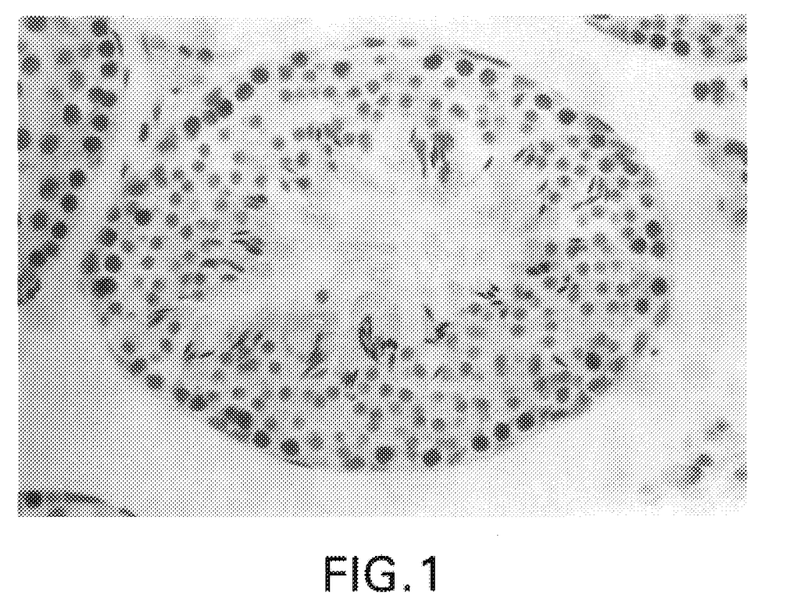
FIGS. 1 and 2 are photographs of cross-sections of seminiferous tubules from the testes of adult mice.
Figure 2:
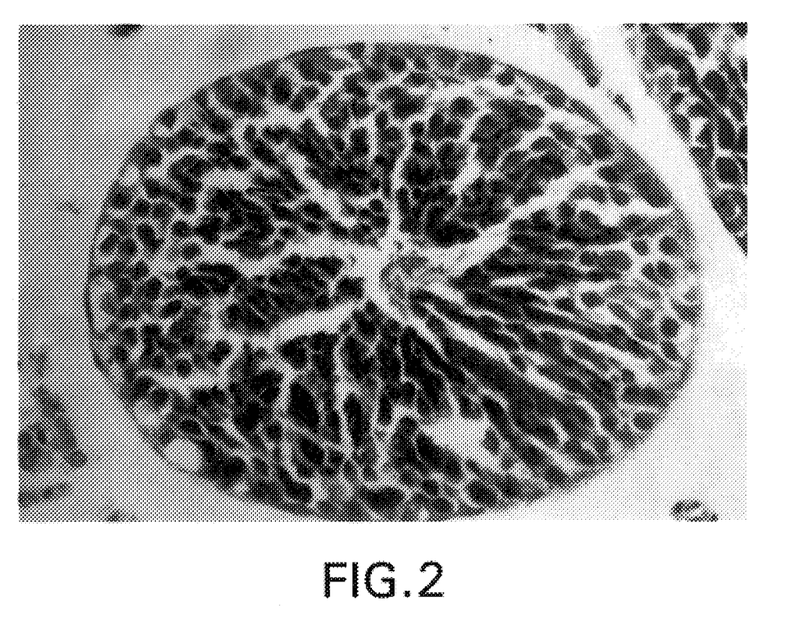

An example of a cross section of a seminiferous tubule from the testis of an adult control mouse not containing the transgene and treated with X-gal is shown in FIG. 1. There are no cells that show blue or dark staining. In contrast, a cross section of a seminiferous tubule from the testis of an adult mouse containing the lacZ transgene and treated with X-gal is shown in FIG. 2. There is intense blue (dark) staining in all the mature stages of spermatogenesis, which occupy the center of the tubule. FIGS. 1 and 2 represent examples of a negative and positive control, respectively. They are referred to below in the experimental descriptions.

The cells for transfer were obtained from neonatal mice (3 to 10 days old) at a time before they would show any stain because of their immature stage of differentiation. These cells are reporter cells and carry the transgene ZF-lacZ; they are obtained from the testes of hybrid mice that carry antigenic determinants from C57BL/6 and SJL mice. The cells were then injected into the seminiferous tubules of recipient or host mice at several sites on the testicular surface.

The recipient mice were of several types as follows:

1. Hybrid mice of C57BL/6 x SJL parent stock. These mice were immunologically tolerant of the donor cells and should not reject them. The host mice were prepared by treatment with Busulfan® to destroy their endogenous sperm cells.

2. Mice that carry the W-mutation. Homozygotes and compound heterozygotes for certain alleles of this gene are completely devoid of sperm cells in the adult. Therefore, any sperm cells in their seminiferous tubules must come from the differentiation of transferred cells. Furthermore, these mice are immunologically incompatible with the donor cell strain of mice because the W-mice are of C57 background and would not be tolerant of the SJL antigens on the surface of cells containing the ZF-lacZ transgene.

3. Inbred mice of the 129/SV strain. These mice are immunologically incompatible with the donor cells because the cells contain C57BL/6 and SJL antigens and 129/SV mice would recognize both strains as foreign. Foreign cells would be rejected and destroyed by a mouse if present in a normal environment, such as a skin or organ graft. However, some parts of the testis, particularly the inner region of the seminiferous tubules, is considered to have a degree of immunological privilege (i.e. They do not reject foreign tissue as readily as other body locations. The uterus is the best example of an immunologically privileged location, since it does not reject the fetus carrying the male antigens).

The implementation and use of the invention has substantiated in the following examples, and the results obtained provided proof of several important aspects of the invention. The examples describing implementation of the invention are as follows.

Experimental

Figure 3A:
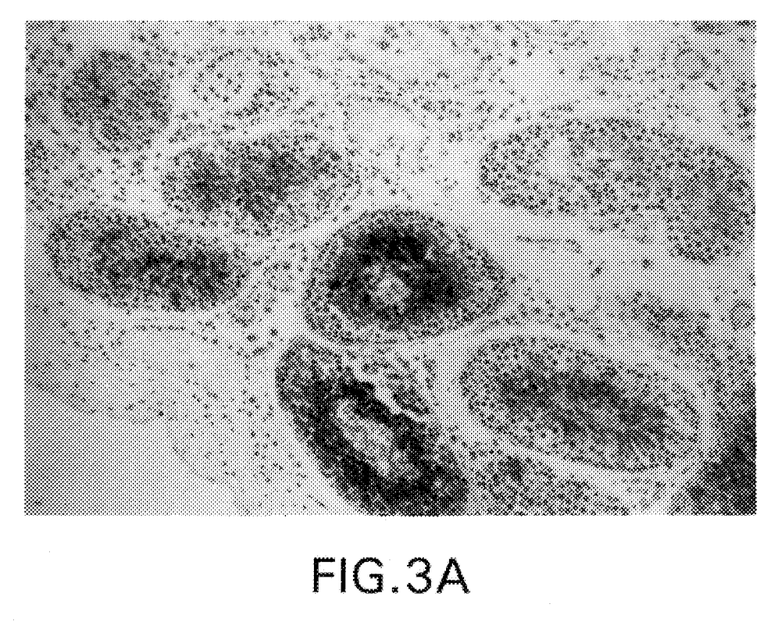
FIGS. 3A–D are photographs of a cross-section of testes, showing blue (dark) stained tubules, demonstrating, survival, differentiation and development of transferred cells that carried the ZFlacZ transgene.
Figure 3B:
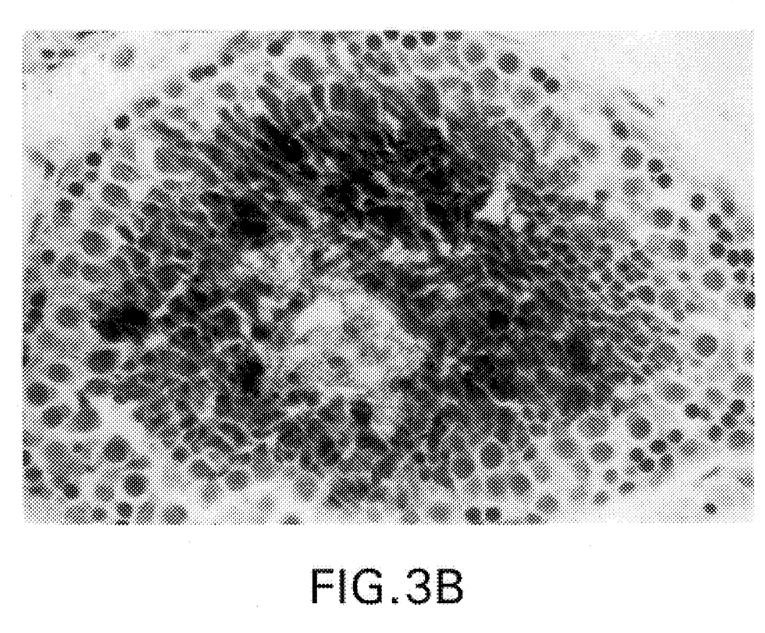

1. Primitive stem cells or spermatogonia can be transferred from one animal into another host animal and the donor cells will survive, divide and differentiate. Cells were taken from neonatal testes of hybrid mice (C57BL/6 x SJL) containing the ZF-lacZ transgene, and these cells were microinjected into the seminiferous tubules of Busulfan® treated hybrid (C57BL/6 x SJL) mice. The host testes were removed at various times (days to months) following the injection and examined for the presence of cells from the donor animal by analyzing the testes for the presence of lacZ staining. A number of animals were found that clearly demonstrated the success of the transfer as well as survival, division and differentiation of the donor cells. In FIG. 3A is shown a cross section from one of these testes, and it is clear that a number of tubules are stained blue (dark). This is the same type staining seen in FIG. 2 and, therefore, represents descendants of donor cells rather than regeneration of endogenous cells, which would not stain but would look like FIG. 1. Furthermore, mature spermatozoa are seen in some tubules. FIG. 3B is a higher magnification of one of the tubules from FIG. 3A. The mature spermatozoa are clearly seen as thin dark nuclei toward the center of the tubule. The blue stain (dark) is very obvious at this magnification. Survival, division and differentiation of donor cells must take place to achieve this result. Donor cells will not stain because they are immature; endogenous cells (should any regenerate) will not stain because they lack the transgene; and no mature spermatozoa were present among the donor cells. A few transferred stem cells divided and differentiated to fill this seminiferous tubule in the host animal.

Figure 3C:
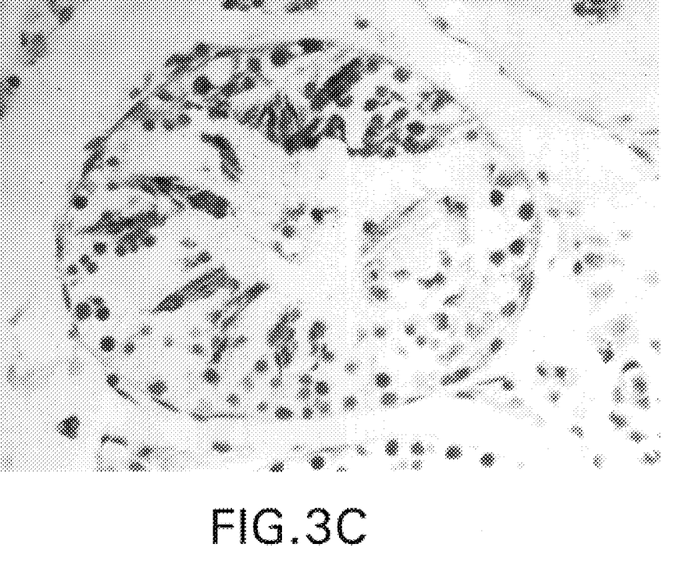

2. In the second implementation of the invention, the same type cells described above, from hybrid mice and carrying the ZF-lacZ transgene, were transferred into the seminiferous tubules of W-mutant mice. These mice are devoid of endogenous sperm cells. The success of the procedure is demonstrated in FIG. 3C which shows a cross section of a tubule that received donor cells. There is blue staining of cells in this cross section demonstrating their derivation from donor cells. Furthermore, this mutant animal is incapable of generating sperm cells. In this embodiment of the invention the donor cells have colonized a completely sterile testis in an animal that is not immunologically tolerant of the donor mouse strain. The testis environment has provided an immunological protection as anticipated in the invention application. The examination of this testis was performed 120 days after donor cell transfer indicating that cell survival, division and differentiation continues in the host for a long period, probably until death.

Figure 3D:
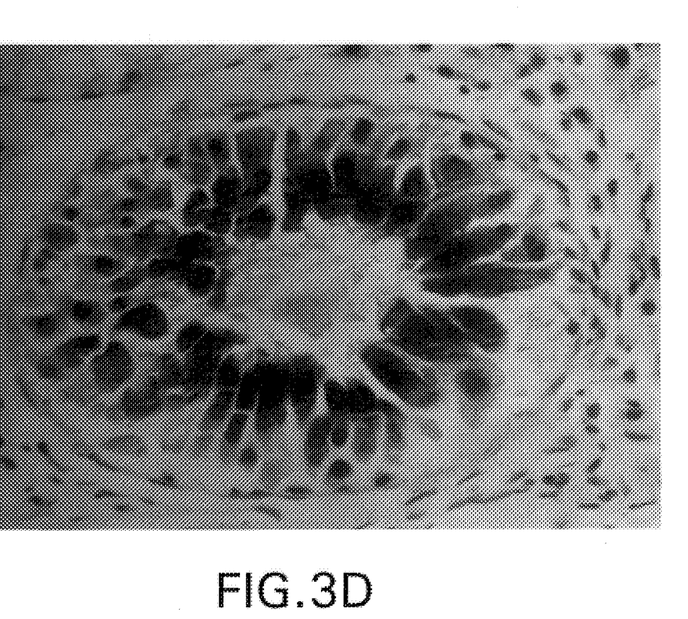

3. In the third implementation of the invention, the same type donor cell was transferred into the seminiferous tubule of a 129/SV inbred mouse. The mouse had previously been treated with Busulfan® to destroy endogenous sperm cells. The result is shown in FIG. 3D. Again the donor cells (stained blue or dark) have colonized this tubule. The differentiation has not proceeded as far as in the examples above; perhaps, because the transfers were among the first performed while improvements were still underway. However, this example demonstrates tolerance of foreign cells in the tubule despite very strong immunological differences. The examination of this testis was performed 110 days after donor cell transfer, indicating a very long period of donor cell survival.

Example B

Material and Methods

Cell Preparation

Male germ cells were isolated from mice of three different ages: between fetal (f) day 18 and postnatal (pn) day 2; between pn days 5 and 15; and between pn days 21 and 28. The basic procedures used have been described (Bellve' et al., (1977) *J. Cell Biol.* 74, 68–85). Several modifications were introduced to increase the number and improve the handling of isolated cells. Briefly, 12 to 40 testes were collected (the larger numbers from the youngest animals), the tunica removed, and the exposed tubules subjected to collagenase (1 mg/ml) treatment followed by trypsin (0.25%) digestion. The released cells were centrifuged at 600×G at 16° for 5 minutes. Following centrifugation, the supernatant was removed and the cells resuspended in injection medium. The composition of the medium was based on a formula originally developed for mouse eggs (Brinster, R. L. (1965) *J. Reprod. Fert.* 10, 227–240) and subsequently modified for use with primordial germ cells (Brinster et al., (1977) *Exptl. Cell Res.* 109, 111–117). These cell types have a requirement or preference for pyruvate and lactate as energy substrates, and male germ cells may share this characteristic because of their origin from primordial germ cells. The composition of the injection medium was: 132 mM NaCl, 7.8 mM $Na_2HPO_4$, 2.6 mM KCl, 1.1 mM $KH_2PO_4$, 0.1 mM EDTA, 0.25 mM pyruvate, 3 mM lactate, 1 mM glutamine, 5.5 mM glucose, 5 mg/ml bovine serum albumin, 200 µg/ml DNAse I, pH 7.4. The cells were resuspended in 1.6 ml of the injection medium, and 400 µl allocated to microcentrifuge tubes on ice. Cell concentration values for different age testes were determined on samples of cells collected in an identical manner on days when injections were not performed. There was variation in cell concentration from day to day resulting from the number of testes available and the age of the donor males. An attempt was made to maximize the number of cells available in order to inject a concentrated solution, since the number of stem cells is unknown but thought to be small. One tube containing 400 µl was used to inject the testes of a single mouse. Before introducing the cell suspension into the injection pipette, 50 µl of filtered trypan blue (4%) was added to the tube and the suspension agitated. The dye allowed visualization of solution flow in the seminiferous tubule and was used to determine the number of dead cells in the injection suspension, which was generally less than 5 percent. It was not possible to measure the volume of cell suspension that entered the tubules, but the percent of surface tubules that filled with solution was recorded for each recipient testis.

Sertoli cells were isolated and maintained according to methods previously described (Karl et al., (1990) *Methods In Enzymology* 190, 71–75). They were added to the germ cells just before injection into the tubules. Embryonic stem cells (AB-1) were a gift from Alan Bradley and were maintained as previously described (Bradley, et al., (1992) *Bio/Technology*, 10, 534–539; Robertson, E. J. (1987) in "Teratocarcinomas and Embryonic Stem Cells: A Practical Approach", ed. Robertson, E. J. (MI Press Limited, Oxford, England), pp. 71–112).

Transplantation Procedure

Two separate protocols were used to transfer donor cells into recipient mice. In protocol 1, donor cells were isolated from the testes of C57BL/6 mice that were homozygous for a dominant mutant that resulted in tan belly hair. These cells were transferred into testes of compound heterozygous or homozygous mutant W mice (designated W/W) which do not show spermatogenesis (reviewed in Silvers, W. K. (1979) *The Coat Colors of Mice: A Model for Mammalian Gene Action and Interaction*. (Springer-Verlag, New York). pp. 206–241). In protocol 2, donor cells were isolated from mice (designated ZFlacZ) that were heterozygous for an *E. coli* β-galactosidase transgene, which allowed round spermatids to be stained blue following incubation with substrate (Zambrowicz, et al., (1994) *Development* 120, 1549–1559). Donor cells from these mice were injected into testes of (C57BL/6 x SJL) F1 males that had been treated with Busulfan® (40 mg/kg intraperitoneally) at 4 to 6 weeks of age. This treatment destroys spermatogenic stem cells (Bucci, et al., (1987) *Mutation Research* 176, 259–268).

Cell Injection

To minimize the number of injection sites and to increase the efficiency of injection concentrated cell suspension, a glass pipette with a 1 mm outside diameter and a 40µ tip was secured in a micropipette holder (WPI Cat. No. MPH6S). The tip of a 1 ml plastic syringe was then inserted into the other end of the micropipette holder, and the syringe was cut at the 0.4 ml mark. The cell solution containing the dye was deposited in the syringe barrel, which was then screwed onto the metal end of an Eppendorf capillary holder attached by tubing to a pressure injector (Eppendorf Model 5242). To expose the tubules, only 1 to 3 small incisions (1–3 mm) were made in the tunica per testis. With these modifications, an average of 80 percent of the surface tubules could be filled with concentrated cell suspension (Table 1).

Analysis of Recipient Testes

To allow donor cells to undergo at least one cycle of spermatogenesis, recipient males were maintained a minimum of 50 days following injection before sacrifice. In protocol 1, the testes were fixed and 5µ microscopic sections cut and stained with hemotoxin and eosin. The number of tubule cross sections showing any stages of spermatogenesis was recorded. In protocol 2, the testes were incubated with 5-bromo-4-chloro-3-indolyl-β-D-galactoside (X-gal) and the number of tubules that stained blue recorded, up to a maximum of 12; beyond this, it was difficult to identify individual tubules because of their tortuous course, and these testes were recorded as 12+. For some mice in protocol 2, microscopic sections were cut and stained with neutral fast red. The number of tubule cross sections that stained blue generally was greater than the number of tubules visibly blue on gross examination. Progeny of recipient males (protocol 2 only) were analyzed by incubating testes with X-gal or by assaying for the presence of the transgene (Zambrowicz, et al., (1994) *Development* 120, 1549–1559).

Results

Donor cells were collected from mouse testes at 3 representative developmental stages. The first, between fetal day 18 and pn day 2, provided primarily gonocytes and mitotically active Sertoli cells. The second, between pn days 5 and 15, provided germ cells and Sertoli cells in transition between the perinatal and adult states. The third, between pn days 21 and 28, provided quiescent Sertoli cells and a germ cell distribution approaching that of mature testes. The average time from cell transplantation to analysis was approximately 90 days, with a range of 54 to 300 days (Table 1). This represented between 2 and 10 spermatogenic cycles. In total, 245 testes were injected with donor cells, of which 173 (71%) showed evidence that transplanted cells had survived, colonized recipient seminiferous tubules, and initiated spermatogenesis (Table 1). Cells isolated from perinatal testes (18 f to 2 pn) colonized 24 of 86 injected tests, with an average of 3 to 4 tubules (out of approximately 150 to 300 visible in a cross section) showing evidence of donor cell spermatogenesis. Donor cells isolated from pn day 5 to 15 and pn day 21 to 28 displayed a greater ability to colonize recipient testes: 90 of 96 and 59 of 63 testes, respectively, showed evidence of donor cell spermatogenesis. Donor cell age and strain (protocol 1 vs 2) both had a significant effect on the number of testes colonized (Table 1). The number of tubules supporting spermatogenesis for the pn day 5 to 15 and 21 to 28 cells was also significantly greater than for the perinatal cells. Although the concentration of donor cells injected was lower for suspensions from perinatal animals, reflecting the small size of donor testes, the percent of surface tubules filled with cell suspension (~80%) and the percent live cells, as indicated by trypan blue, were similar for all 3 donor stage cell preparations.

TABLE 1

Spermatogonial Stem Cell Transplantation into Recipient Testes

| Donor Cell Age* (Days) | Concentration of Donor Cells+ (× 10$^6$) | Donor Cell Strain‡ | Testes Injected | Percent Surface Area Covered§ | Time to Analysis¶ | Tests with Donor Cells‖ | Tubules with Donor Cells** |
|---|---|---|---|---|---|---|---|
| 18 f–2 pn | 35 ± 16 [10–51] | C57BL/6 | 46 | 78 ± 20 [30–100] | 81 ± 20 [54–130] | 6 (13) | 3.5 ± 2.3 [1–7] |
|  |  | ZFlacZ | 40 | 73 ± 21 [40–100] | 81 ± 14 [60–110] | 18 (45) | 3.2 ± 2.5 [1–9] |
| 5 pn–15 pn | 71 ± 18 [44–108] | C57BL/6 | 47 | 80 ± 19 [30–100] | 117 ± 64 [70–300] | 41 (87) | 14.5 ± 16.2 [1–70] |
|  |  | ZFlacZ | 49 | 80 ± 15 [50–100] | 87 ± 37 [60–197] | 49 (100) | 8.1 ± 4.0 [1–12+] |
| 21 pn–28 pn | 83 ± 32 [45–123] | C57BL/6 | 11 | 86 ± 7 [75–95] | 99 ± 43 [70–180] | 7 (64) | 16.7 ± 6.4 [9–26] |
|  |  | ZFlacZ | 52 | 83 ± 15 [40–100] | 80 ± 25 [60–155] | 52 (100) | 5.1 ± 3.4 [1–12+] |

Table I are: Mean ± S.D.; Range is in brackets,
*Donor cell mice of three ages provided testis cells for transfer into recipients. f, fetal; pn, post natal.
+Number of determinations of cell concentration was 6 for 18 f–2 pn, 9 for 5 pn–15 pn, 6 for 21 pn–28 pn.
‡C57BL/6 testis cells were transferred to the seminiferous tubules of homozygous or compound heterozygous W/W mice that lack spermatogenesis (protocol 1). ZFlacZ testis cells from mice of C57BL/6 × SJL genotype were transferred to the seminiferous tubules of (C57BL/6 × SJL) F1 hybrid mice in which endogenous spermatogenesis had been destroyed by Busulfan ® treatment (protocol 2). ZFlacZ mice were heterozygous for a transgene (–3.5 kb cEMS177/lacZ), and the transgenic lines were designated TgN(c177lacZ) 226Bri and TgN (c177lacZ) 227Bri (Zambrowicz, et al., (1994) Development 120, 1549–1559).
§Percent of the surface seminiferous tubules in the recipient testis filled by the injected cell suspension.
¶Number of days from injection of donor cells to analysis of the recipient testis for presence of spermatogenesis. This represents the time available for donor cell proliferation.
‖Effect of donor cell age and donor cell strain (C57BL/6 vs ZFlacZ) were both significant by analysis of variance (0.05 > P > 0.01).
**Number of tubules with spermatogenesis in those recipient testes that had evidence of donor cell colonization. In C57BL/6 donor cell recipients, the number of tubule cross sections with evidence of spermatogenesis were counted. In ZFlacZ donor cell recipients, the number of individual tubules stained, blue were counted up to a maximum of 12. Tubules in testes with more than 12 stained could not be accurately counted. Therefore, in this column the values for C57BL/6 cells are not directly comparable to those for ZFlacZ cells. The difference between the C57BL/6 values for the 18 f–2 pn age group and the other two groups was significant (P < 0.001). The difference between the ZFlacZ values for the, 18 f–2 pn age group and the 5 pn–15 pn age group was significant (P < 0.001), and the difference between the 18 f–2 pn age group and the 21 pn–28 pn age group was also significant (0.02 > P > 0.01). Analyses by t-test. The ZFlacZ statistical comparisons underestimate the true difference, because in testes with 12+ tubules staining the exact number of tubules with spermatogenesis is too great to count accurately.

Figure 4A:
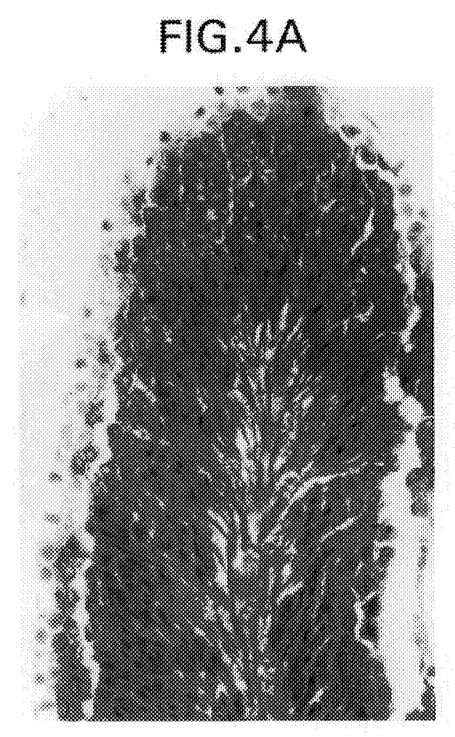
Figure 4B:
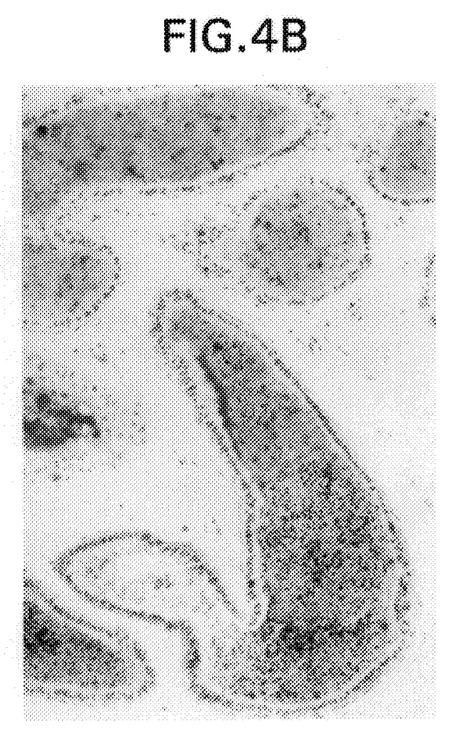

Following colonization of recipient seminiferous tubules, donor cells generally established a morphological pattern representative of normal spermatogenesis. For protocol 1, all stages of sperm cell differentiation could be identified in microscopic cross sections of the seminiferous tubules. None of these stages was seen in control testes not injected with cells, because there is no endogenous spermatogenesis in W mice, or in tubules of injected testes not populated with donor cells. Likewise, ZFlacZ donor cells (protocol 2) established normal spermatogenesis in Busulfan®-treated recipients with typical sperm cell associations and morphology of the tubules, and mature spermatozoa were produced (FIG. 4A). The testes of mice injected with Busulfan® but not receiving donor cells do not generally have tubules with spermatogenesis (Bucci, et al., (1987) *Mutation Research* 176, 259–268). In mice receiving a lower dose of Busulfan® (e.g., if there was leakage at the time of injection) some tubules could be repopulated by surviving endogenous stem cells. However, these tubules would be distinct, since round spermatids and subsequent stages derived from endogenous stem cells do not stain blue with X-gal. The success of the transferred donor cells in colonizing the recipient testis varied, and some testes from ZFlacZ mice demonstrated up to 100 cross sections containing various stages of spermatogenesis. In testes with the most extensive colonization, by either C57BL/6 or ZFlacZ donor cells, mature spermatozoa were transported to the epididymis (FIG. 4B). No sperm were seen in epididymal tubules when recipient testes were not colonized by donor cells.

Figure 5A:
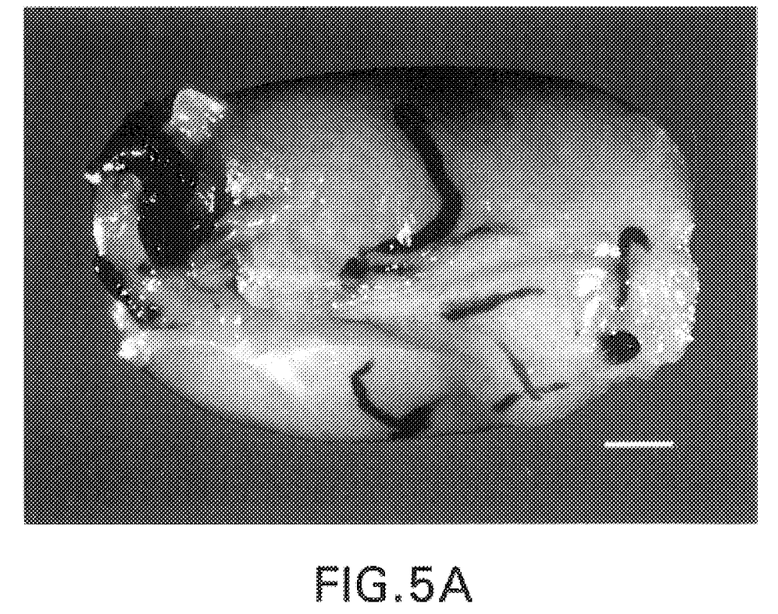
Figure 5B:
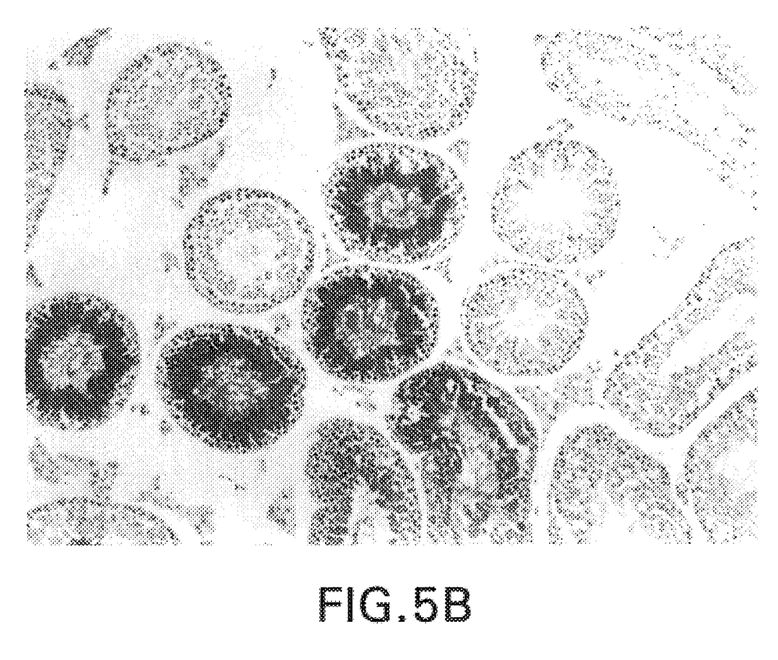
Figure 6:
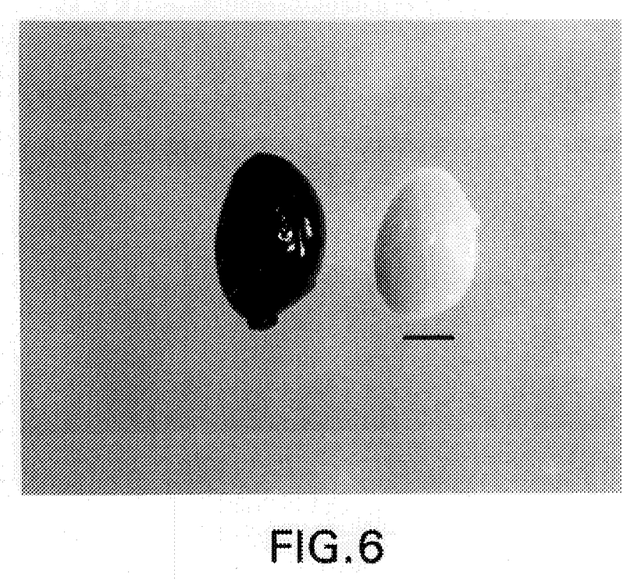

As anticipated based upon the observation of spermatozoa in the epididymides of some experimental mice, spermatozoa could also be identified in the ejaculate of these recipient males. Initially, the number of spermatozoa was insufficient to result in progeny. An approach to produce fertile production of offspring from donor-derived spermatozoa would be to provide carrier spermatozoa. As a consequence of occasional Busulfan® leakage at the time of injection or variability of individual animal susceptibility, a few experimental recipients may acquire fertility following tubule repopulation by endogenous stem cells. If donor cells have also become established, a fraction of tubules with spermatogenesis will stain blue (FIGS. 5A, B), and the ejaculate will contain spermatozoa derived from endogenous and transplanted stem cells. One-half the male progeny that develop from eggs fertilized with spermatozoa of ZFlacZ donor stem cell origin should have testes that stain blue with X-gal, because transferred ZFlacZ cells are heterozygous for the transgene. Testes from progeny of a recipient in which spermatogenesis occurred from endogenous and transplanted stem cells are shown in FIG. 6; however, only one of 122 male offspring carried the transgene. To specifically generate recipients that would reestablish endogenous spermatogenesis, protocol 2 was used; ten males were treated with 30 mg/kg Busulfan®, and the testes injected with donor cells from pn day 5 to 15 or 21 to 28 mice. Testes of seven were examined 65 to 290 days after injection. All were enlarged relative to animals treated with 40 mg/kg Busulfan®, indicating a significant level of spermatogenesis. The testes contained 8.2±4.0; (mean±standard deviation M±SD) blue staining tubules. Of the 3 remaining males, one that received pn day 5 to 15 cells is still infertile, one that received pn day 21 to 28 cells has sired 6 of 39 transgenic progeny, and the third that receiving pn day 5 to 15 cells has sired 6 of 15 transgenic progeny. Offspring were born beginning approximately 8 months after donor cell injection. With this approach, up to 80 percent of the progeny of the male with the most successful colonization are from donor-derived spermatozoa, half of which carry the transgene.

Although injected cell suspension contained donor Sertoli cells, several experiments were performed in which Sertoli cells ($10^5$ to $10^7$) isolated as described were added to the donor cell suspension to determine if this would enhance repopulation. Using protocol 1 and donor cells from pn day 5 to 15 mice, 10 to 12 recipient testes demonstrated spermatogenesis, with 13.0±12.7 (M±SD) tubule cross sections colonized per testis. With protocol 2 and the same age donor cells, 24 of 25 testes had stained tubules with 9.0±3.7 (M±SD) tubules stained per testis. The average time of analysis of the recipients after donor cell injection was 112 days. In general, the degree of colonization with and without additional Sertoli cells was similar (compare to Table 1).

Discussion

Figure 7:
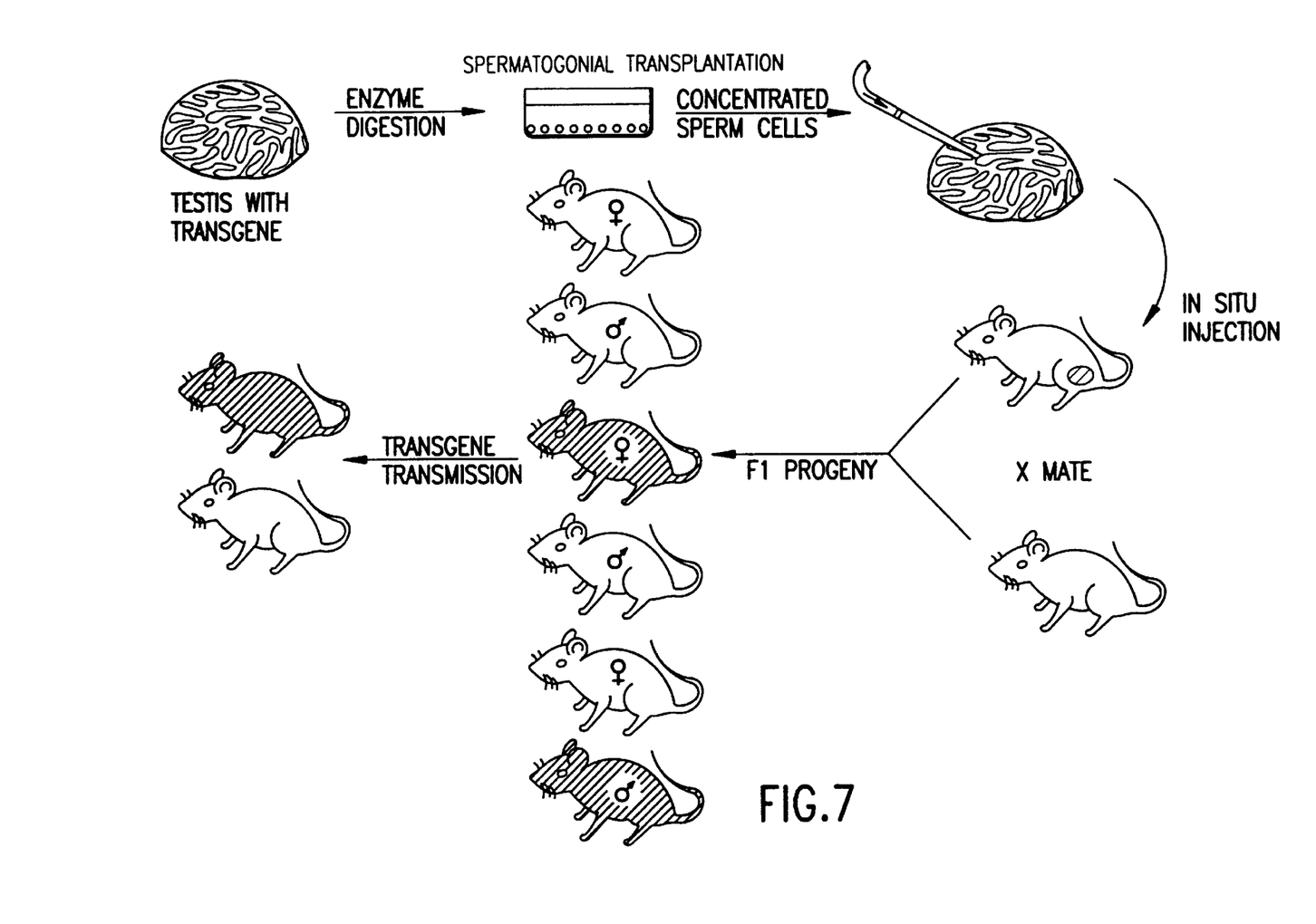
FIG. 7 is a diagram of the procedure used in example B.

The studies described above demonstrate that stem cells can be harvested from donor testes, maintained in vitro, transferred to a recipient testis, establish normal spermatogenesis, and produce functional spermatozoa that fertilize eggs and result in offspring. The production of young from the transplanted spermatogonial stem cells and the high percent of recipient spermatozoa arising from the transplanted cells indicates that colonization of the seminiferous tubules can be very effective. The procedure used in the above example shown diagrammatically in FIG. 7.

In these studies, donor cell populations were mixed, containing Sertoli cells and various stages of differentiating sperm cells that varied with the age of the donor testes (Bellve', A. R. (1979) in Oxford Reviews of Reproductive Biology, ed. Finn, C. A. (Clarendon Press, Oxford, England) Vol. 1, pp. 159–261; de Kretser, et al (1998) in The Physiology of Reproduction, eds. Knobil, E. & Neill, J. (Raven Press, Ltd., New York) pp. 837–932; Bellve' et al., (1977) J. Cell Biol. 74, 68–85). Among this diverse group of cell types, only cells with stem cell potential could initiate spermatogenesis. Spermatocytes, meiotic stages, and spermatids are not capable of self-renewal. Thus, even if donor cells representing later stages of spermatogonia established an interaction with recipient Sertoli cells and continued to differentiate, they would become fully mature and be shed into the lumen by 35 days post-transfer (de Kretser, et al (1998) in The Physiology of Reproduction, eds. Knobil, E. & Neill, J. (Raven Press, Ltd., New York, N.Y.) pp. 837–932; Russell, et al., (1990) in Histological and Histopathological Evaluation of the Testis, (Cache River Press, Clearwater, Fla.) pp. 1–40). Spermatogenic elements visible in recipient testes after this time would necessarily have arisen from donor cells with stem cell potential.

The age of the testes from which donor cells were isolated had an influence on the efficiency of colonization of recipient testes. At birth the germ cells are gonocytes, but during the first week of life these cells differentiate into spermatogonia, which divide and begin to differentiate (Bellve', A. R. (1979) in Oxford Reviews of Reproductive Biology, ed. Finn, C. A. (Clarendon Press, Oxford, England) Vol. 1, pp. 159–261; de Kretser, et al (1998) in The Physiology of Reproduction, eds. Knobil, E. & Neill, J. (Raven Press, Ltd., New York) pp. 837–932). Thereafter, the spermatogonial cell population expands and differentiating stages of spermatogenesis appear successively. In prepubertal mice this first wave of spermatogenesis is synchronized, with spermatocytes appearing at about day 10, spermatids at about day 20, and mature spermatozoa at about day 35 (de Kretser, et al (1998) in The Physiology of Reproduction, eds. Knobil, E. & Neill, J. (Raven Press, Ltd., New York) pp. 837–932; Bellve' et al., (1977) J. Cell Biol. 74, 68–85). Sertoli cells also undergo changes during this period. They continue to divide until between 10 and 14 days after birth, after which they become mitotically quiescent (Gondos, et al., (1993) in The Sertoli Cell, eds. Russell, L. D. & Griswold, M. D. (Cache River Press, Clearwater, Fla.) pp. 116–154). Thus, by recovering donor cells at birth, pn day 5 to 15, and pn day 21 to 28, three different mixed cell populations were tested for stem cell potential. Surprisingly, the results suggest that gonocytes, despite their primitive stage of development, were less efficient as donor cells than older populations of cells containing spermatogonia. However, it has not been determined whether the stem cell populations in the 3 developmental stages tested have a differential sensitivity to the harvesting protocol employed. Although the number of dead cells as indicated by trypan blue staining was similar for the 3 cell preparations, differential killing of small populations of stem cells may not have been detectable. Also, stem cells are likely to make up a different fraction of the total cell population at each stage (Bellve', A. R. (1979) in Oxford Reviews of Reproductive Biology, ed. Finn, C. A. (Clarendon Press, Oxford, England) Vol. 1, pp. 159–261; de Kretser, et al (1998) in The Physiology of Reproduction, eds. Knobil, E. & Neill, J. (Raven Press, Ltd., New York) pp. 837–932; Russell, et al., (1990) in Histological and Histopathological Evaluation of the Testis, (Cache River Press, Clearwater, Fla.) pp. 1–40.). These factors may also account for the lower efficiency of C57BL/6 donor cells in colonizing recipients. However, an additional element in this effect could be an inferior ability of the tubules in W recipients to support spermatogenesis.

Spermatogenesis was morphologically normal in many tubules examined (Russell, et al., (1990) in Histological and Histopathological Evaluation of the Testis, (Cache River Press, Clearwater, Fla.) pp. 1–40), indicating effective colonization of seminiferous tubules. The donor cell population contained both germ cells and Sertoli cells; therefore, it has not yet been determined whether the interacting Sertoli-spermatogonial units that established a spermatogenic colony and repopulated the tubule were composed of donor germ cells interacting with endogenous Sertoli cells, with transferred Sertoli cells, or both. However, when additional Sertoli cells were coinjected with germ cells they did not have a dramatic effect on colonization efficiency. This suggests that Sertoli cells were not a limiting factor, and may indicate that endogenous Sertoli cells were adequate to support recolonization.

The most striking result of these experiments was production of offspring from donor cell-derived spermatozoa.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A method of making a non-human mammal harboring a biologically functional non-native cell comprising:
  (i) selectively destroying the endogenous germ cell population in the seminiferous tubules of a first non-human mammal, leaving intact the supporting cells comprising Sertoli cells in said tubules; and (ii) colonizing said seminiferous tubules of said first non-human mammal with spermatogonia from a second non-human mammal of the same species as the first non-human mammal, wherein said colonizing comprises injecting a solution containing said spermatogonia from said second mammal into said seminiferous tubules or into the lumen of the rete testes into the efferent duct leading into the epididymis of said first mammal, wherein following colonization, said spermatogonia from second mammal produce spermatozoa which are capable of repopulating said seminiferous tubules, fertilizing ova, and producing viable offspring.

2. The method of claim 1, wherein said step (i) comprises subjecting said tubules to a physical treatment.

3. The method of claim 2, wherein said physical treatment is radiation treatment.

4. The method of claim 1, wherein said step (i) comprises subjecting said tubules to a chemical treatment.

5. The method of claim 1, in which said seminiferous tubules contain no biologically functional endogenous germ cells.

6. The method of claim 1, wherein said non-human mammal is a mouse.

7. The method of claim 1, wherein said non-human mammal is a farm animal.

8. A method of harboring a biologically functional non-native germ cell comprising:

(i) selectively destroying the endogenous germ cell population in the seminiferous tubules of a first rodent, leaving intact the supporting cells comprising Sertoli cells in said tubules; and (ii) colonizing said seminiferous tubules of said first rodent with spermatogonia from a second rodent, wherein said colonizing comprises injecting a solution containing said spermatogonia from said second rodent into said seminiferous tubules or into the lumen of the rete testes or into the efferent duct leading into the epididymis of said first rodent, wherein following colonization, said spermatogonia from second rodent produce spermatozoa which are capable of repopulating said seminiferous tubules, fertilizing ova, and producing viable offspring.

9. The method of claim 8, wherein said step (i) comprises subjecting said tubules to a physical treatment.

10. The method of claim 8, wherein said physical treatment is radiation treatment.

11. The method of claim 8, wherein said step (i) comprises subjecting said tubules to a chemical treatment.

12. The method of claim 8, in which said seminiferous tubules contain no biologically functional endogenous germ cells.

13. The method of claim 8, wherein said non-human mammal is a mouse.

14. A method of making a non-human mammal comprising (i) selectively destroying the endogenous germ cell population in the seminiferous tubules of a first non-human mammal, leaving intact the supporting cells comprising Sertoli cells in said tubules; and (ii) colonizing said seminiferous tubules of said first non-human mammal with spermatogonia from a second non-human mammal of the same species as the first non-human mammal, wherein said colonizing comprises injecting a solution containing said spermatogonia from said second mammal into said seminiferous tubules or into the lumen of the rete testes into the efferent duct leading into the epididymis of said first mammal, wherein following colonization, said spermatogonia from second mammal produce spermatozoa which are capable of repopulating said seminiferous tubules, fertilizing ova, and producing viable offspring; and breeding the non-human harboring a non-native germ cell.

15. A method of comprising (i) selectively destroying the endogenous germ cell population in the seminiferous tubules of a first rodent, leaving intact the supporting cells comprising Sertoli cells in said tubules; and (ii) colonizing said seminiferous tubules of said first rodent with spermatogonia from a second rodent, wherein said colonizing comprises injecting a solution containing said spermatogonia from said second rodent into said seminiferous tubules or into the lumen of the rete testes or into the efferent duct leading into the epididymis of said first rodent, wherein following colonization, said spermatogonia from second rodent produce spermatozoa which are capable of repopulating said seminiferous tubules, fertilizing ova, and producing viable offspring; and breeding the rodent harboring a non-native germ cell.

* * * * *